United States Patent
McClelland et al.

(10) Patent No.: US 11,727,820 B2
(45) Date of Patent: *Aug. 15, 2023

(54) SYSTEM AND METHOD FOR OBTAINING METADATA ABOUT CONTENT STORED IN A REPOSITORY

(71) Applicant: D2L Corporation, Kitchener (CA)

(72) Inventors: Phillip McClelland, Kitchener (CA); Philip Brown, Kitchener (CA); Chris Carleton, Kitchener (CA)

(73) Assignee: D2L Corporation, Kitchener (CA)

( * ) Notice: Subject to any disclaimer, the term of this patent is extended or adjusted under 35 U.S.C. 154(b) by 132 days.

This patent is subject to a terminal disclaimer.

(21) Appl. No.: 17/075,835

(22) Filed: Oct. 21, 2020

(65) Prior Publication Data

US 2021/0134168 A1 May 6, 2021

Related U.S. Application Data

(63) Continuation of application No. 14/086,045, filed on Nov. 21, 2013, now Pat. No. 10,849,850.

(51) Int. Cl.
| | |
|---|---|
| *G09B 5/00* | (2006.01) |
| *G09B 7/02* | (2006.01) |
| *G06F 16/2457* | (2019.01) |
| *A61K 9/00* | (2006.01) |

(Continued)

(52) U.S. Cl.
CPC .............. *G09B 5/00* (2013.01); *A61K 9/0051* (2013.01); *A61K 31/498* (2013.01); *A61K 47/34* (2013.01); *G06F 16/24573* (2019.01); *G09B 7/02* (2013.01)

(58) Field of Classification Search
None
See application file for complete search history.

(56) References Cited

U.S. PATENT DOCUMENTS

| | | | |
|---|---|---|---|
| 7,788,207 B2 | 8/2010 | Alcorn et al. | |
| 9,536,436 B2 * | 1/2017 | Venkataramani | ......... H04L 9/40 |
| 2006/0010096 A1 | 1/2006 | Crossland et al. | |

(Continued)

OTHER PUBLICATIONS

Mary S. Woodley, "Crosswalk, Metadata harvesting, Federated Searching, Metasearching: Using Meradara to Connect Users and Information", Introduction to Metadata 3.0, 2008, 25 pages.

(Continued)

*Primary Examiner* — Uyen T Le
(74) *Attorney, Agent, or Firm* — Bereskin & Parr LLP/S.E.N.C.R.L.,s.r.l.

(57) ABSTRACT

At least one of the embodiments described herein relate generally to a method of obtaining metadata for content stored in a first repository. The method may be performed at a second repository, and may include the acts of: identifying a content object stored in the first repository, the content object comprising learning content usable in an electronic educational system to provide electronic learning; identifying metadata for the content object stored in the first repository, the metadata associated with the learning content of the content object; retrieving the metadata associated with the learning content from the first repository; and storing a harvested content object corresponding to the content object, wherein the harvested content object includes the metadata associated with the learning content of the content object stored in the first repository.

20 Claims, 9 Drawing Sheets

(51) Int. Cl.
    *A61K 31/498*    (2006.01)
    *A61K 47/34*     (2017.01)

(56) References Cited

U.S. PATENT DOCUMENTS

| | | | |
|---|---|---|---|
| 2007/0099161 A1 | 5/2007 | Krebs et al. | |
| 2008/0254429 A1* | 10/2008 | Woolf | G09B 7/02 706/45 |
| 2008/0261191 A1* | 10/2008 | Woolf | G09B 7/00 434/323 |
| 2009/0031215 A1 | 1/2009 | Collier, II et al. | |
| 2009/0035733 A1 | 2/2009 | Meitar et al. | |
| 2009/0106234 A1 | 4/2009 | Siedlecki et al. | |
| 2009/0234784 A1 | 9/2009 | Buriano et al. | |
| 2010/0094886 A1 | 4/2010 | Krebs et al. | |
| 2010/0131505 A1 | 5/2010 | Erickson | |
| 2011/0010210 A1 | 1/2011 | Alcorn et al. | |
| 2011/0065082 A1 | 3/2011 | Gal et al. | |
| 2011/0145293 A1 | 6/2011 | Stewart | |
| 2011/0212430 A1 | 9/2011 | Smithmier et al. | |
| 2012/0148999 A1* | 6/2012 | Baker | G09B 7/00 434/362 |
| 2013/0157242 A1* | 6/2013 | Leonardo | G09B 7/00 434/322 |
| 2014/0272892 A1 | 9/2014 | Rozycki et al. | |

OTHER PUBLICATIONS

Hatala et al., "The EduSource Communication Language: Implementing Open Network for Learning Repositories and Services", 2004 ACM Symposium on Applied Computing, 6 pages.

\* cited by examiner

```xml
<?xml version="1.0" encoding="utf-8"?>
<dc xmlns="http://schemas.companyA.com/metadata/cpp/companyA.xsd"
xmlns:xml="http://www.w3.org/XML/1998/namespace">
<!-- Dublin Core Elements -->
<creator>NASA/Stennis Space Center</creator>
<description>This historical section of the Swamp to Space exhibit in John C. Stennis Space Center's Stennisphere tells the story of and pays tribute to the families who moved their homes to make way for the space age in Mississippi. Names of the 2,202 Hancock County families are listed on two columns in the exhibit.</description>
<format>JPEG</format>
<format>JPEG Thumb</format>
</format>
<identifier>http://archive.org/details/00-042-324</identifier>
<rights>Public Domain</rights>
<source>http://www.ssc.nasa.gov/sirs/</source>
<subject>Stennisphere exhibit, Swamp to Space, Stennis history</subject>
<subject>where -- Stennis Space Center (SSC)</subject>
<subject>where -- Mississippi</subject>
<title>Swamp to Space historical exhibit</title>

<!-- Extended metadata describing learning content -->
<thumbnailurl>http://www.companyA.com/thumbnails/0019498432.png</thumbnailurl>
<lmsType>Topic</lmsType>
<relatedobject>
  <description xml:lang="en-ca">
    My parent topic
  </description>
  <url>http://www.companyA.com/stuff/assets/topic00384.html</url>
  <relation>parent</relation>
</relatedobject>
<usageData>
  <reviewsurl>http://www.companyA.com/stuff/assets/reviews/00384</reviewsurl>
  <timesAccessed>9420</timesAccessed>
  <rating>4.7</rating>
</usageData>
</dc>
```

FIG. 6

```xml
<?xml version="1.0" encoding="utf-8"?>
<xs:schema targetNamespace="http://schemas.companyA.com/metadata/cpp/companyA.xsd"
    elementFormDefault="qualified"
    xmlns="http://schemas.companyA.com/metadata/cpp/companyA.xsd"
    xmlns:xml="http://www.w3.org/XML/1998/namespace"
    xmlns:xs="http://www.w3.org/2001/XMLSchema"
    xmlns:dc="http://purl.org/dc/elements/1.1/">

<xs:import namespace="http://www.w3.org/XML/1998/namespace" schemaLocation="http://www.w3.org/2001/03/xml.xsd" />
    <xs:import namespace="http://purl.org/dc/elements/1.1/"
        schemaLocation="http://dublincore.org/schemas/xmls/qdc/2008/02/11/dc.xsd" />

<!-- Controlled vocabulary for object relations. -->
    <xs:simpleType name="objectRelation">
        <xs:restriction base="xs:string">
            <xs:enumeration value="Parent" />
            <xs:enumeration value="Child" />
            <xs:enumeration value="Previous" />
            <xs:enumeration value="Next" />
            <xs:enumeration value="Related" />
            <!-- should handle basic navigation needs. -->
        </xs:restriction>
    </xs:simpleType>

<!-- Controlled vocabulary for the <lmsType> element -->
    <xs:simpleType name="lmsType">
        <xs:restriction base="xs:string">
            <xs:enumeration value="Course" />
            <xs:enumeration value="Topic" />
            <xs:enumeration value="Quiz" />
            <xs:enumeration value="Discussion" />
            <!-- Add others as necessary. -->
        </xs:restriction>
    </xs:simpleType>

<xs:complexType name="usageData">
        <xs:sequence>
            <xs:element name="reviewsUrl" type="xs:anyURI" minOccurs="0" maxOccurs="1" />
            <xs:element name="timesAccessed" type="xs:positiveInteger" minOccurs="0" maxOccurs="1" />
            <xs:element name="rating" type="xs:float" minOccurs="0" maxOccurs="1" />
        </xs:sequence>
    </xs:complexType>

<xs:complexType name="objectDescription">
        <xs:complexContent mixed="true">
            <xs:restriction base="xs:anyType">
                <xs:attribute ref="xml:lang" use="optional" />
            </xs:restriction>
        </xs:complexContent>
    </xs:complexType>
```

FIG. 7A

```xml
<xs:complexType name="relatedobject">
  <xs:sequence>
    <xs:element name="description" minoccurs="0" maxoccurs="unbounded" type="objectDescription" />
    <xs:element name="url" type="xs:anyURI" minOccurs="0" maxOccurs="1" />
    <xs:element name="relation" type="objectRelation" />
  </xs:sequence>
</xs:complexType>

<!-- The root element. -->
<xs:complexType name="companyA">
  <xs:choice minoccurs="0" maxoccurs="unbounded">
    <!-- Import Dublin Core elements -->
    <xs:element ref="dc:contributor" />
    <xs:element ref="dc:coverage" />
    <xs:element ref="dc:creator" />
    <xs:element ref="dc:date" />
    <xs:element ref="dc:description" />
    <xs:element ref="dc:format" />
    <xs:element ref="dc:identifier" />
    <xs:element ref="dc:language" />
    <xs:element ref="dc:publisher" />
    <xs:element ref="dc:relation" />
    <xs:element ref="dc:rights" />
    <xs:element ref="dc:source" />
    <xs:element ref="dc:subject" />
    <xs:element ref="dc:title" />
    <xs:element ref="dc:type" />

<!-- Start of learning content elements -->
    <xs:element name="thumbnailurl" type="xs:anyURI" />
    <xs:element name="lmstype" type="lmsType" />
    <xs:element name="usageData" type="usageData" />
    <xs:element name="relatedobject" type="relatedobject" />
  </xs:choice>
</xs:complexType>
<xs:element name="dc" type="companyA" />
</xs:schema>
```

FIG. 7B

SYSTEM AND METHOD FOR OBTAINING METADATA ABOUT CONTENT STORED IN A REPOSITORY

CROSS-REFERENCE TO RELATED PATENT APPLICATION

This application is a continuation of U.S. patent application Ser. No. 14/086,045, filed on Nov. 21, 2013. The complete disclosure of U.S. patent application Ser. No. 14/086,045 is incorporated herein by reference.

FIELD

The described embodiments relate generally to systems and methods of obtaining metadata about content stored in a repository.

INTRODUCTION

A repository (also called a digital library or a digital archive) can store content containing media (e.g., articles, videos, etc.) that is retrievable by external sources. As the various content items stored in a repository may be individually retrievable, the term "content object" will be used herein to generally refer to a single data item that may be retrieved from a repository. To facilitate the organization and retrieval of the content objects, the repository may also store metadata describing the content objects.

The metadata available on a repository may be indexed and collected by an external repository. In this manner, the metadata collected by the external repository may be considered to be "harvested", so as to allow the external repository to store a metadata content object (also called a "harvested" content object) that corresponds to the content object stored in the first repository. When the external repository itself is subsequently searched (e.g., by a user computing device attempting to locate available content objects), the external repository may be able to provide search results that include both harvested content objects and content objects that are stored locally on the external repository.

Electronic educational systems may provide repositories that allow users to select content objects that are available for inclusion into online learning experiences. Typically, such content objects may contain specialized learning content (e.g., information indicating that the content object is a quiz or an assessment) that may not be adequately described as an attribute of the content object.

SUMMARY

In one aspect, in at least one example embodiment described herein, there is provided a method of obtaining metadata for content stored in a first repository. The method may be performed at a second repository, and may include the acts of: identifying a content object stored in the first repository, the content object comprising learning content usable in an electronic educational system to provide electronic learning; identifying metadata for the content object stored in the first repository, the metadata associated with the learning content of the content object; retrieving the metadata associated with the learning content from the first repository; and storing a harvested content object corresponding to the content object, wherein the harvested content object includes the metadata associated with the learning content of the content object stored in the first repository.

In at least one embodiment, the method further includes: generating information from the metadata describing the learning content of the content object; and if the harvested content object is located in a search for content objects performed at the second repository, providing the generated information along with the harvested content object in the search results so that when the search results are displayed, the generated information for the harvested content object is displayed in a substantially similar manner as when corresponding information is displayed for local content objects stored at the second repository.

In at least one embodiment, the retrieving of the metadata may be performed using a modified version of the Open Archives Initiative Protocol for Metadata Harvesting (OAI-PMH) protocol, in which the modified version includes an Extensible Markup Language (XML) schema that extends metadata items provided in the OAI-PMH protocol to include the metadata associated with the learning content.

In at least one embodiment, the learning content may include a Learning Management System (LMS) type of the content object.

In at least one embodiment, the method may further includes: recognizing the LMS type of the harvested content object as being the LMS type of the content object; determining an action that can be performed for the harvested content object based on the LMS type; and performing the action for the harvested content object. For example, the LMS type may include an assessment, and the action may include integrating the harvested content object into a LMS gradebook. In various embodiments, the action is the same as that which would be performed for a local content object that is also of the LMS type, stored at the second repository.

In at least one embodiment, the learning content may include usage information for the content object.

In at least one embodiment, the learning content may include relationship information for the content object with respect to one or more other content objects. For example, the relationship information for the content object may include structure information that indicates that the content object contains, or the content object is contained within, the one or more other content objects. For example, the relationship information for the content object may include sequence information that indicates that the content object is recommended to be used before or after the one or more other content objects. For example, the relationship information for the content object may include information indicating that the content object and the one or more other content objects are members of a same collection of content objects.

In at least one embodiment, the learning content may include at least one of: information indicating an instructor using the content object; information about a student who is able to access the content object; information indicating a course using the content object; and information indicating an institution using the content object.

In another aspect, in at least one example embodiment described herein, there is provided a computer-readable medium that stores instructions for obtaining metadata for content stored in a first repository. When the instructions are executed by a processor of a server hosting a second repository, the processor is configured to: identify a content object stored in the first repository, the content object comprising learning content usable in an electronic educational system to provide electronic learning; identify metadata for the content object stored in the first repository, the metadata associated with the learning content of the content object; retrieve the metadata associated with the learning content from the first repository; and store a harvested content object corresponding to the content object, wherein the harvested content object includes the metadata associated with the learning content of the content object stored in the first repository.

In another aspect, in at least one example embodiment described herein, there is provided a server comprising a memory that is configured to store instructions for hosting a second repository that obtains metadata for content stored in a first repository, and a processor that is coupled to the memory. When the instructions are executed by the processor, the processor is configured to: identify a content object stored in the first repository, the content object comprising learning content usable in an electronic educational system to provide electronic learning; identify metadata for the content object stored in the first repository, the metadata associated with the learning content of the content object; retrieve the metadata associated with the learning content from the first repository; and store a harvested content object corresponding to the content object, wherein the harvested content object includes the metadata associated with the learning content of the content object stored in the first repository.

In at least one embodiment, the processor may be further configured to: generate information from the metadata associated with the learning content of the content object; and if the harvested content object is located in a search for content objects performed at the second repository, provide the generated information along with the harvested content object in the search results so that when the search results are displayed, the generated information for the harvested content object is displayed in a substantially similar manner as when corresponding information is displayed for local content objects stored at the second repository.

In at least one embodiment, the retrieving of the metadata may be performed using a modified version of the Open Archives Initiative Protocol for Metadata Harvesting (OAI-PMH) protocol, the modified version including an Extensible Markup Language (XML) schema that extends metadata items provided in the OAI-PMH protocol to include the metadata associated with the learning content.

In at least one embodiment, the learning content may include a Learning Management System (LMS) type of the content object.

In at least one embodiment, the processor may be further configured to: recognize the LMS type of the harvested content object as being the LMS type of the content object; determine an action that can be performed for the harvested content object based on the LMS type; and perform the action for the harvested content object. For example, the LMS type may include an assessment, and the action may include integrating the harvested content object into a LMS gradebook. In various embodiments, the action may be the same as that which would be performed for a local content object that is also of the LMS type, stored at the second repository.

In at least one embodiment, the learning content may include usage information for the content object.

In at least one embodiment, the learning content may include relationship information for the content object with respect to one or more other content objects. For example, the relationship information for the content object may include structure information that indicates that the content object contains, or the content object is contained within, the one or more other content objects. For example, the relationship information for the content object may include sequence information that indicates that the content object is recommended to be used before or after the one or more other content objects. For example, the relationship information for the content object may include information indicating that the content object and the one or more other content objects are members of a same collection of content objects.

In various embodiments, the learning content may include at least one of: information indicating an instructor using the content object; information about a student who is able to access the content object; information indicating a course using the content object; and information indicating an institution using the content object.

In one aspect, in at least one example embodiment described herein, there is provided a method of providing metadata for content stored at a first repository. The method may include: providing a content object at the first repository, the content object comprising learning content usable in an electronic educational system to provide electronic learning; providing metadata at the first repository, the metadata associated with the learning content of the content object; and transmitting the metadata associated with the learning content to a second repository, wherein the second repository stores a harvested content object corresponding to the content object, and wherein the harvested content object includes the metadata associated with the learning content of the content object.

In various embodiments, the second repository generates information from the metadata associated with the learning content of the content object, and if the harvested content object is located in a search for content objects performed at the second repository, the second repository provides the generated information along with the harvested content object in the search results so that when the search results are displayed, the generated information for the harvested content object is displayed in a substantially similar manner as when corresponding information is displayed for local content objects stored at the second repository.

DRAWINGS

For a better understanding of the various embodiments described herein, and to show more clearly how these various embodiments may be carried into effect, reference will be made, by way of example, to the accompanying drawings which show at least one example embodiment, and which are now described.

FIG. 6 is an example of metadata for a content object in the form of an Extensible Markup Language (XML) file, in accordance with at least one example embodiment; and FIGS. 7A and 7B show an example of a schema file that indicates how the data in the XML file of FIG. 6 may be structured, in accordance with at least one example embodiment.

Figure 1:
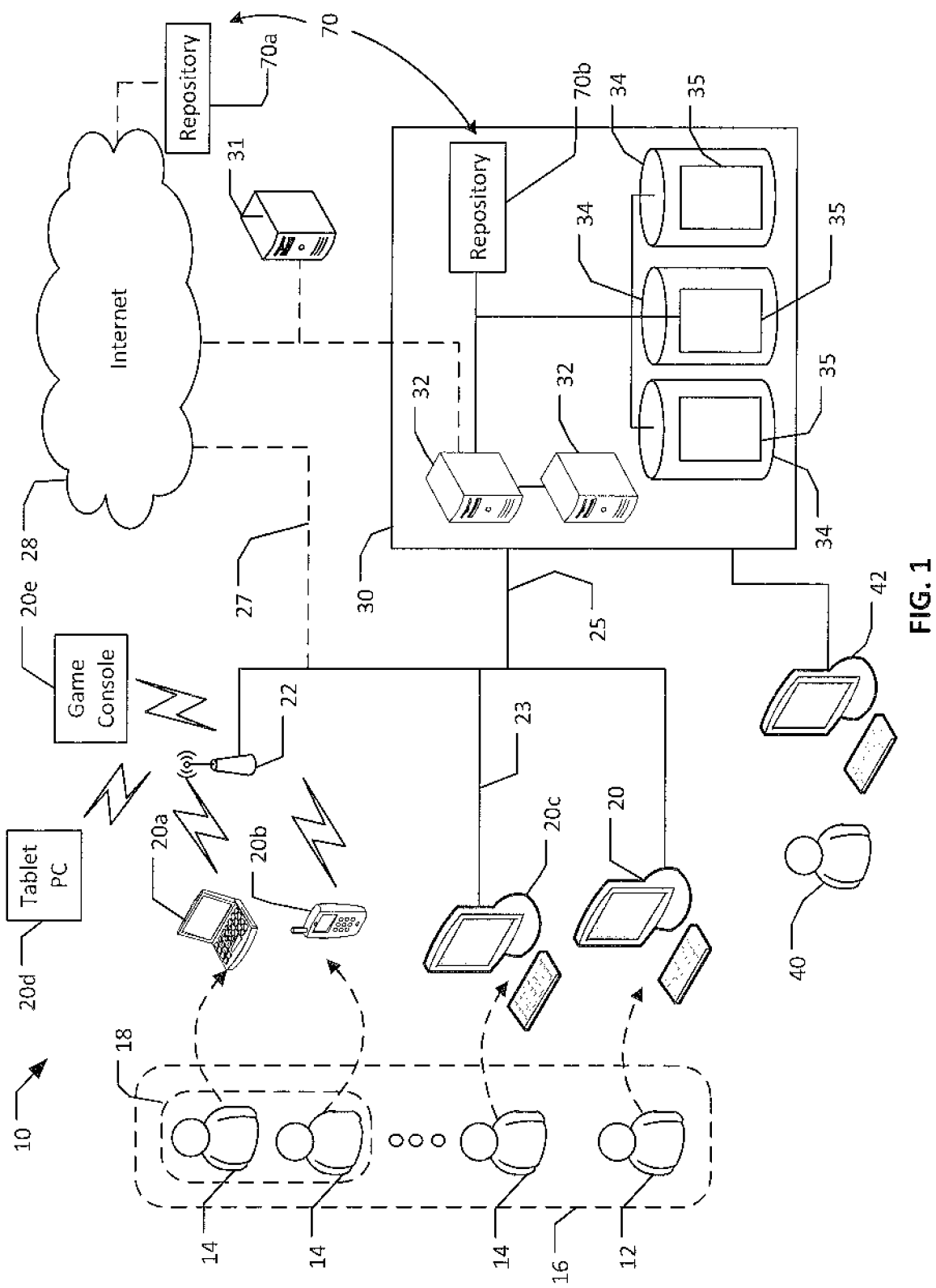
FIG. 1 is a block diagram illustrating an educational system for providing electronic learning in accordance with at least one example embodiment.

Further aspects and advantages of the embodiments described herein will appear from the following description taken together with the accompanying drawings.

DETAILED DESCRIPTION

Various apparatuses or processes will be described below to provide an example of an embodiment of each claimed subject matter. No embodiment described below limits any claimed subject matter and any claimed subject matter may cover processes or apparatuses that differ from those described below. The claimed subject matter are not limited to apparatuses or processes having all of the features of any one apparatus or process described below or to features common to multiple or all of the apparatuses or processes described below. It is possible that an apparatus or process described below is not an embodiment of any claimed subject matter. Any subject matter disclosed in an apparatus or process described below that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the example embodiments described herein in any way, but rather as merely describing the implementation of various embodiments as described.

In some cases, the example embodiments of the systems and methods described herein may be implemented in hardware or software, or a combination of both. In some cases, the example embodiments described herein may be implemented in one or more computer programs, executing on one or more programmable computing devices comprising at least one processor, a data storage system (including volatile and non-volatile memory and/or storage elements), at least one input device (e.g. a keyboard, mouse or touch-screen), and at least one output device (e.g. a display screen, a printer, a wireless radio and the like).

For example, and without limitation, the programmable computers may include servers, personal computers, laptops, tablets, personal data assistants (PDA), cell phones, smart phones, gaming devices, and other mobile devices. Program code can be applied to input data to perform the functions described herein and to generate output information. The output information can then be supplied to one or more output devices for outputting to one or more users.

In some example embodiments described herein, each program may be implemented in a high level procedural or object oriented programming and/or scripting language or both. Accordingly, the program code may be written in C, C++, Java, SQL or any other suitable programming language and may include modules or classes, as is known to those skilled in object oriented programming. However, other programs may be implemented in assembly, machine language or firmware as needed. In either case, the language may be a compiled or interpreted language.

The computer programs may be stored on a storage media (e.g. a computer readable medium such as, but not limited to, ROM, magnetic disk, optical disc) or a device that is readable by a general or special purpose computing device. The program code, when read by the computing device, configures the computing device to operate in a new, specific and predefined manner in order to perform at least one of the methods described herein.

Furthermore, some of the programs associated with the systems and methods of the embodiments described herein are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

It should also be noted that the terms "coupled" or "coupling" as used herein can indicate that two elements or devices can be directly connected to one another or connected to one another through one or more intermediate elements or devices via an electrical element or electrical signal depending on the particular context.

The embodiments described herein generally relate to systems and methods for obtaining metadata for the learning content provided in content objects stored in a repository. In various embodiments, the content objects having such learning content may be called a "learning object". Such learning objects may be used in an electronic educational system to, for example, better allow users to select content for inclusion in an online course. In various embodiments, a repository available to be accessed in an electronic educational system may also be called a "Learning Object Repository" (LOR).

An overview of an example electronic educational system will now be discussed.

Referring now to FIG. 1, shown therein is an example embodiment of an educational system 10 for providing electronic learning. One or more users 12 and 14 can use the educational system 10 to communicate with an educational service provider 30 to participate in, create, and consume electronic learning services, including various educational courses. In some cases, the educational service provider 30 may be part of or associated with a traditional "bricks and mortar" educational institution (e.g. an elementary school, a high school, a university or a college), another entity that provides educational services (e.g. an online university, a company that specializes in offering training courses, or an organization that has a training department), or may be an independent service provider (e.g. for providing individual electronic learning). Therefore, it should be understood that a course is not limited to formal courses offered by formal educational institutions. The course may include any form of learning instruction offered by an entity of any type. For example, the course may be a training seminar at a company for a small group of employees or a professional certification program with a larger number of intended participants (e.g. PMP, CMA, etc.).

In some embodiments, one or more educational groups can be defined that involve one or more of the users 12 and 14. For example, as shown in FIG. 1, the users 12 and 14 may be grouped together in an educational group 16 representative of a particular course (e.g. History 101, French 254), in which the user 12 is an "instructor" and is responsible for providing the course (e.g. organizing lectures, preparing assignments, creating educational content, etc.), while the other users 14 are "learners" that consume the course content, e.g. the users 14 are enrolled in the course to learn the course content. As used herein, the term "instructor device" may generally refer to a computing device that an "instructor" is using when he or she is accessing the educational system 10.

In some cases, the users 12 and 14 may be associated with more than one educational group. For instance, the users 14 may be enrolled in more than one course and the user 12 may be enrolled in at least one course and may be responsible for teaching at least one other course or the user 12 may be responsible for teaching more than one course.

In some cases, educational sub-groups may also be formed. For example, two of the users 14 are shown as part of an educational sub-group 18. The sub-group 18 may be formed in relation to a particular project or assignment (e.g. sub-group 18 may be a lab group) or based on other criteria. In some cases, due to the nature of the electronic learning, the users 14 in a particular sub-group 18 need not physically meet, but may collaborate together using various tools provided by the educational service provider 30.

In some cases, the groups 16 and sub-groups 18 could include users 12 and 14 that share common interests (e.g. interests in a particular sport), that participate in common activities (e.g. users that are members of a choir or a club), and/or have similar attributes (e.g. users that are male, users under twenty-one years of age, etc.).

Communication between the users 12 and 14 and the educational service provider 30 can occur either directly or indirectly using any suitable computing device. For example, the user 12 may use a computing device 20 such as a desktop computer that has at least one input device (e.g. a keyboard and a mouse) and at least one output device (e.g. a display screen and speakers).

The computing device 20 can generally be any suitable device for facilitating communication between the users 12 and 14 and the educational service provider 30. For example, the computing device 20 could be a laptop 20a wirelessly coupled to an access point 22 (e.g. a wireless router, a cellular communications tower, etc.), a wirelessly enabled personal data assistant (PDA) 20b or smart phone, a terminal 20c over a wired connection 23 or a tablet computer 20d or a game console 20e over a wireless connection.

The computing devices 20 may be connected to the service provider 30 via any suitable communications channel. For example, the computing devices 20 may communicate to the educational service provider 30 over a local area network (LAN) or intranet, or using an external network, such as, for example, by using a browser on the computing device 20 to browse one or more web pages presented over the Internet 28 over a data connection 27.

The wireless access points 22 may connect to the educational service provider 30 through a data connection 25 established over the LAN or intranet. Alternatively, the wireless access points 22 may be in communication with the educational service provider 30 via the Internet 28 or another external data communications network. For example, one user 14 may use a laptop 20a to browse to a webpage that displays elements of an electronic learning system (e.g. a course page).

In some cases, one or more of the users 12 and 14 may be required to authenticate their identities in order to communicate with the educational service provider 30. For example, the users 12 and 14 may be required to input a login name and/or a password or otherwise identify themselves to gain access to the educational system 10.

In other cases, one or more users (e.g. "guest" users) may be able to access the educational system 10 without authentication. Such guest users may be provided with limited access, such as the ability to review only one or a few components of the course, for example, to decide whether they would like to participate in the course.

The educational service provider 30 generally includes a number of functional components for facilitating the provision of social electronic learning services. For example, the educational service provider 30 generally includes one or more processing devices 32 (e.g. servers), each having one or more processors. The processing devices 32 are configured to send information (e.g. HTML or other data) to be displayed on one or more computing devices 20, 20a, 20b and/or 20c in association with social electronic learning (e.g. course information). In some cases, the processing device 32 may be a computing device 20 (e.g. a laptop or a personal computer).

The educational service provider 30 also generally includes one or more data storage devices 34 (e.g. memory, etc.) that are in communication with the processing devices 32, and could include a relational database (such as an SQL database), or other suitable data storage devices. The data storage devices 34 are configured to host data 35 about the courses offered by the service provider. For example, the data 35 can include course frameworks, educational materials to be consumed by the users 14, records of assessments of users 14, assignments done by the users 14, as well as various other databases and the like.

The data storage devices 34 may also store authorization criteria that define which actions may be taken by the users 12 and 14. In some cases, the authorization criteria may include at least one security profile associated with at least one role. For example, one role (e.g., an "instructor" role) could be defined for users who are primarily responsible for developing an educational course, teaching it, and assessing work product from students of the course. Users with such a role may have a security profile that allows them to configure various components of the course to add content objects to lessons or topics, to post assignments, to add assessments, to evaluate performance, and so on.

In some cases, some of the authorization criteria may be defined by specific users 40 who may or may not be part of the educational community 16. For example, users 40 may be permitted to administer and/or define global configuration profiles for the educational system 10, define roles within the educational system 10, set security profiles associated with the roles, and assign roles to particular users 12 and 14 who use the educational system 10. In some cases, the users 40 may use another computing device (e.g. a desktop computer 42) to accomplish these tasks.

The data storage devices 34 may also be configured to store other information, such as personal information about the users 12 and 14 of the educational system 10, information about which courses the users 14 are enrolled in, roles to which the users 12 and 14 are assigned, particular interests of the users 12 and 14 and the like.

The processing devices 32 and data storage devices 34 may also provide other electronic learning management tools (e.g. allowing users to add and drop courses, communicate with other users using chat software, etc.), and/or may be in communication with one or more other vendors that provide the tools.

In various embodiments, an education service provider 30 may also include a repository 70. The repository 70 may be a database that is accessed by an application that is executing on an existing processing device 32 at the educational service provider 30. Additionally or alternatively, a separate computing device may host the repository 70. As illustrated in FIG. 1, the educational service provider 30 includes a separate repository 70*b*.

The repository 70*b* may store content objects that are local to the educational service provider 30. However, as will be discussed below, the repository 70*b* may also index and retrieve (e.g., "harvest") metadata about content objects that are stored on a repository 70 that is remote from the repository 70*b*. For example, the repository 70*b* may index and retrieve metadata from a remote repository 70*a* that is provided on a server that is remote from the educational service provider 30.

In some cases, the educational system 10 may also have one or more backup servers 31 that may duplicate some or all of the data 35 stored on the data storage devices 34. The backup servers 31 may be desirable for disaster recovery to prevent undesired data loss in the event of an electrical outage, fire, flood or theft, for example.

In some cases, the backup servers 31 may be directly connected to the educational service provider 30 but located within the educational system 10 at a different physical location. For example, the backup servers 31 could be located at a remote storage location that is some distance away from the service provider 30, and the service provider 30 could connect to the backup server 31 using a secure communications protocol to ensure that the confidentiality of the data 35 is maintained.

Figure 2:
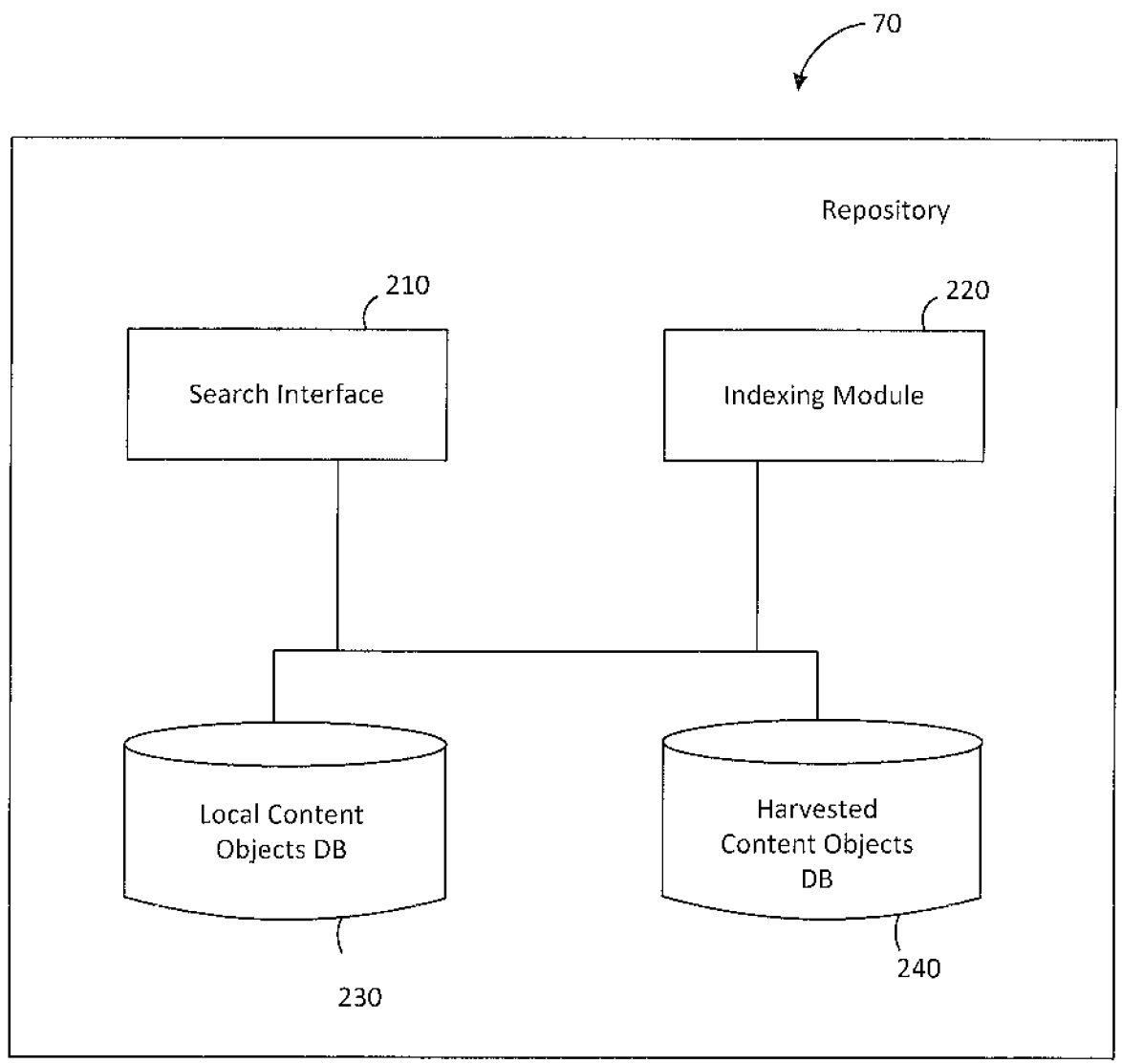
FIG. 2 is a block diagram illustrating components of a repository, in accordance with at least one example embodiment.

Referring now to FIG. 2, shown there generally as 70 is a block diagram illustrating components of a repository, in accordance with at least one example embodiment described herein. As discussed above, the repository 70 may be provided in the context of an educational service provider 30 (e.g., accessible by an application executing on a processing device 32 or another physical server) or it may be remote from a given educational service provider 30. For ease of explanation, FIG. 2 illustrates a simplified version of the repository 70 with a limited number of components. However, it will be understood that in alternative embodiments the repository 70 may also include other modules or components that perform additional background functions not discussed herein. As illustrated, the repository 70 may include a search interface 210, an indexing module 220, a local content objects database 230, and a harvested content objects database 240.

The search interface 210 may be an Application Programming Interface (API) that is accessible by an external computing device 20 in the educational system 10 to locate available content objects at the repository 70. For example, the search interface 210 may be accessed by an instructor who is organizing an online course in the educational system 10, and who desires to select content objects for inclusion into a given topic in an online course. To initiate the search, an instructor may enter search terms into a computing device 20, and the computing device 20 may communicate with the search interface 210 of the repository 70 to search the local content objects database 230 and/or the harvested content objects database 240 for content objects having certain types of content. In various embodiments, the search interface 210 may be provided as a computing resource available over Hypertext Transfer Protocol (HTTP), for example.

The indexing module 220 may be configured to index and retrieve (e.g., "harvest") metadata about content objects that are stored on a remote repository 70*a*. Once this metadata is retrieved, the repository 70 may be able to store the retrieved metadata as a harvested content object that describes the content object on the remote repository 70*a*. As used herein, the term "harvested content object" refers generally to the retrieved metadata, as stored by a given repository, that references an actual content object that is stored on a remote repository.

Conventionally, to index the content objects stored in a remote repository, a given repository may use the Open Archives Initiative Protocol for Metadata Harvesting (OAI-PMH) protocol to retrieve metadata about the object. However, the data retrieved using the OAI-PMH protocol may not fully describe the learning content stored on the remote repository 70*a* because the OAI-PMH protocol is intended for general use and is not configured to describe the specific features of a content object that allows it to be used in the educational system 10 for electronic learning purposes. Examples of types of such "learning content" data that would not be described using the OAI-PMH include: links to different retrieval options for a given content object; information indicating that a given content object is of a particular Learning Management System (LMS) type (e.g., a quiz, topic, assessment, course); information describing the relationship between a given content object and another content object; information about other content objects associated with or related to the given content object; and/or usage data for a given content object.

In various embodiments, the relationship information for a given content object may include: structure information such as whether one content object is contained within another content object (e.g., a given child topic being contained within an associated parent topic), sequence information relating to whether one content object is recommended to be used before or after another content object (e.g., a given lesson that should be accessed prior to another lesson), and/or whether one content object is associated with another object by virtue of both objects being members of the same collection (e.g., a given lesson being grouped together with another lesson in a given collection).

Also, in various embodiments, the usage data for a given content object may include 'Reviews' for the content object that may have been provided by previous users of the content object, 'Feedback' for the content object containing suggestions for improvement of the content object provided by previous users; a 'Ratings' value for the content object; and/or a 'Times Accessed' value for the content object. Additionally or alternatively, the usage data may also include information about the users using the content object such as: information indicating the instructor(s) using the content object, information about other student(s) who are able to access the content object, information about (or links to) particular course(s) using the content object, or information indicating the institution(s) using the content object. As will be understood, the term usage data and usage information may be used interchangeably herein. In certain situations where the usage data/information includes numerical data, the usage data/information may also be referred to as usage statistics.

In the example embodiments described herein, the indexing module 220 is configured to retrieve extended metadata describing learning content of a content object. In accordance with the teachings herein, the extended metadata may be beyond that which is provided for in the OAI-PMH protocol. As discussed below, this may allow the extended metadata to be stored in a harvested content object. An example of the extended metadata that may be retrieved and stored is discussed in greater detail below with respect to FIGS. 6 and 7.

The repository 70 may also include a local content objects database 230 and a harvested content objects database 240. The local content objects database 230 may store content objects that are local to the repository 70. When storing local content objects, the local content objects database 230 may store the content (e.g., media such as articles, videos, etc.) encapsulated in the local content objects, as well as metadata that describes such content.

The harvested content objects database 240 typically stores the harvested content objects that have been retrieved from a remote repository 70a. The harvested content objects database 240 may store the metadata describing the content, but typically does not store the actual content of the content object. This is because such content would remain on the remote repository 70a when the metadata for the harvested content object is retrieved.

The search interface 210 may allow a search to be performed of both the local content objects stored in the local content objects database 230, as well as the harvested content objects stored in the harvested content objects database 240. While illustrated as two separate databases, it will be understood that in various embodiments, the local content objects 230 and the harvested content objects 240 may be stored together in a single database, or via some other storage mechanism altogether (e.g., as files on a file system). In various embodiments, repositories 70 that store harvested content objects may be referred to as a "metadata repository" and/or a "harvested repository".

Figure 3:
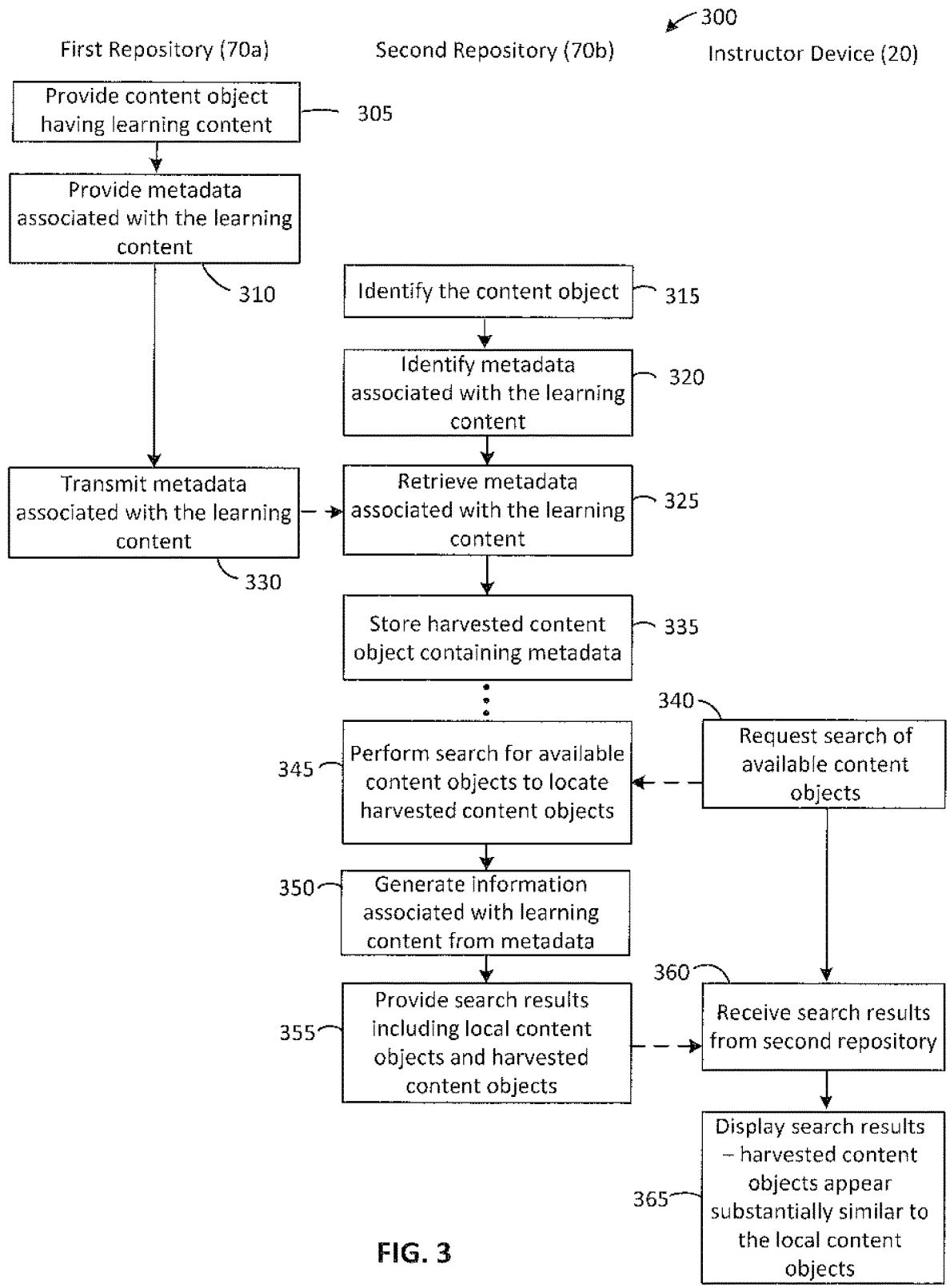
FIG. 3 is a flow chart diagram illustrating interactions between a first repository, a second repository, and an instructor device when the instructor device searches for available content objects on the second repository, in accordance with at least one example embodiment.

Storing Harvested Content Objects that Contain Metadata Associated with Learning Content Referring now to FIG. 3, shown there generally as 300 is a flow chart diagram illustrating example interactions between a first repository 70a, a second repository 70b, and an instructor device when the instructor device searches for available content objects on the second repository 70b, in accordance with at least one example embodiment described herein. As illustrated, the first repository 70a may be considered a "source" repository that provides the content objects that are being indexed and retrieved by the second repository 70b, which can be considered the "recipient" repository that receives the harvested content objects.

At 305, the first repository 70a may provide a content object comprising learning content usable in an electronic educational system 10. As noted above, the learning content may be data that is specifically usable in an educational system for inclusion in an electronic learning experience, and is generally not describable using existing data elements provided in the OAI-PMH protocol. To provide the content object, an owner of the first repository 70a may create content that can be consumed in the educational system. After having created such content, the content may be stored as a content object in the local contents objects database 230 (e.g., as is shown in FIG. 2).

In various embodiments, the content stored in a content object can be educational information on any subject and may be structured to include content in any combination of text, video, audio clips and the like. For example, a content object may contain one or more electronic files. The electronic files can include, but are not limited to, word processing documents, spreadsheets, presentation documents (e.g. Microsoft™ PowerPoint™ files), web pages, Portable Document Format (PDF) documents, a search index of an organization's content, database content, pictures, as well as user generated content from various sources such as discussion forums, emails, and reports. Additionally, the electronic files can be of a file type that is used in electronic learning environments. For example, such file types may include quizzes, quiz questions, assessments, components of assessment components, and/or interactive learning content such as learning games. As will be understood, these types of electronic files may be made interoperable with a learning provider 30 (as shown in FIG. 1) through standardized protocols such as the Sharable Content Object Reference Model (SCORM) and/or a proprietary protocol. In various embodiments, the electronic learning files may be provided using a multimedia and software platform such as Adobe™ Flash™.

At 310, the first repository may provide metadata that is associated with the learning content of the content object (e.g., the metadata may contain data that describes the learning content). As noted above, the metadata may be structured according to a modified version of the OAI-PMH protocol that extends the conventional data elements used with the OAI-PMH protocol. These additional data elements may include attributes for identifying and organizing the different types of learning content that are available in accordance with the teachings herein.

To provide the metadata, the first repository may first identify the properties of the content of the content object that is desired to be described by the metadata. For example, these properties may include user feedback information or retrieval options for the content object (as is described in greater detail below). The metadata may be formatted according to the extended version of the standard OAI-PMH protocol data elements discussed below with respect FIGS. 6 and 7. In various embodiments, the metadata may be stored in this format in a local content objects database 230 (as is shown in FIG. 2). Alternatively, the metadata may be stored in a local format, and the first repository may be able to dynamically convert the stored metadata into the metadata format of FIGS. 6 and 7 in response to harvester requests.

At 315, the second repository 70b may identify one of the content objects that is stored in the first repository 70a and has learning content that is of interest. In various example embodiments, the act of identifying may be performed using the harvesting aspects of the existing OAI-PMH protocol that a given repository may implement to discover the presence of content objects stored in a remote repository 70a. For example, the identifying of the content objects may be performed by web robots implemented on the second repository 70b that are configured to search for content objects from remote repositories 70a.

Additionally or alternatively, the identifying may not be the result of any searching performed by the second repository 70b. For example, the second repository 70b may simply follow a link to a content object that is stored on the first repository 70a to identify content objects. The link may have been inputted into the second repository 70b by a user, for example, if a user is attempting to retrieve the extended metadata for a specific content object stored on the remote repository 70a that the user is already aware of (e.g., if a curator for the second repository 70b decides to feature certain links to content objects stored on the first repository 70a that he/she is independently aware of). Additionally or alternatively, the second repository may be a "federated" repository which does not actively search for metadata from source repositories 70a, but instead simply forwards a searcher's query to a source repository 70a upon receiving a search request. In such cases, the second repository 70b may identify content objects on the first repository 70a when the first repository 70a returns search results in response to a forwarded search request.

At 320, the second repository 70b may identify metadata that is stored at the first repository 70a and is associated with (e.g., describes) the learning content of the identified content object. At 325, the second repository 70b may retrieve the identified metadata associated with the learning content from the first repository 70a.

As noted, the metadata describing the learning content may be provided in a format that extends the conventional data elements of the OAI-PMH protocol in accordance with the teachings herein. While the traditional OAI-PMH protocol may allow the second repository 70b to discover the presence of the content object at the first repository 70a, it may not sufficiently describe the specific learning content that is provided in the content object. An extended version of the OAI-PMH protocol, such as the example that is shown in FIGS. 6 and 7, may allow the first repository 70a to capture information about the learning content of a content object so as to provide such information to the second repository 70b when the second repository 70b attempts to harvest the content object from the first repository 70a.

At 330, the first repository 70a may transmit the metadata associated with (e.g., describes) the learning content for the identified content object to the second repository 70b.

At 335, the second repository 70b stores a harvested content object corresponding to the identified content object stored on the first repository 70a. Having received the metadata describing the learning content from the first repository 70a, the second repository 70b may then store a harvested content object that includes the metadata describing the learning content of the content object.

Providing Harvested Content Objects in Search Results

Referring still to FIG. 3, at some time subsequent to the storing of the harvested content object at the second repository 70b, the harvested content object may be available to be searched when an instructor device 20 in the educational system 10 attempts to locate content objects that are available on the second repository 70b.

At 340, an instructor device 20 may request a search to be performed for available content objects on the second repository 70b. For example, the searching may be to locate content objects that are suitable for adding to a topic in an online course that the instructor is organizing.

After the request is transmitted to the second repository 70b, at 345, the second repository 70b may perform the search for available content objects. As noted above, the request may be received at the second repository 70b via the search interface 210 discussed with respect to FIG. 2. During the search for content objects, both local content objects that are stored locally on the second repository 70b, and harvested content objects (e.g., as may have been retrieved from the first repository 70a) can be located.

For the harvested content objects that are located in the search, at 350, the second repository 70b may generate information associated with (e.g., describing) the learning content of the harvested content object from the metadata. When generating this information, the second repository 70b may process the metadata describing the learning content of the harvested content object according to a schema that indicates the structure of the metadata to extract the information from the metadata. Referring briefly to FIG. 6, shown there is example metadata that contains a description of learning content of an example harvested content object. The metadata illustrated in FIG. 6 is formatted according to the schema shown in FIGS. 7A and 7B. To extract and generate the information describing the learning content from the metadata shown in FIG. 6, the second repository 70b may process the data provided in the XML file of FIG. 6 according to the schema shown in FIGS. 7A and 7B, for example. FIGS. 6, 7A, and 7B will be discussed in greater detail below.

At 355, the second repository 70b may provide the search results to the instructor device 20. The search results may include local content objects that are stored locally on the second repository 70b, the harvested content objects, as well as the generated information describing the learning content of the harvested content objects.

At 360, the instructor device 20 receives the search results from the second repository 70b.

At 365, the instructor device 20 may display or otherwise output the search results received from the second repository 70b. Conventionally, if the second repository 70b had retrieved the harvested content objects (hereafter referred to as conventional harvested content objects) from the first repository 70a solely using data descriptors provided in the OAI-PMH protocol, the resulting conventional harvested content object stored on the second repository 70b would lack information describing the learning content of the content object. When such a conventional harvested content object is returned in search results and displayed, the conventional harvested content object will generally be displayed in a simplistic way that does not provide any information about the learning content of the content object which forces the instructor or user to manually obtain the content object from the first repository 70a and visually inspect the content object in order to determine the subject matter and/or format of the content object.

However, in the method illustrated in FIG. 3, since the second repository 70b received metadata describing the learning content of the harvested content object from the first repository 70a, the search results can contain information describing the learning content (as generated from the metadata describing the learning content). Accordingly, the instructor device 20 may then be able to display information describing the learning content in the search results to the user or instructor which allows the user or instructor to more easily and efficiently search for and use content objects in a course, or other material, that the user or instructor is creating (which may be online or be provided as a hard-copy).

Figure 4:
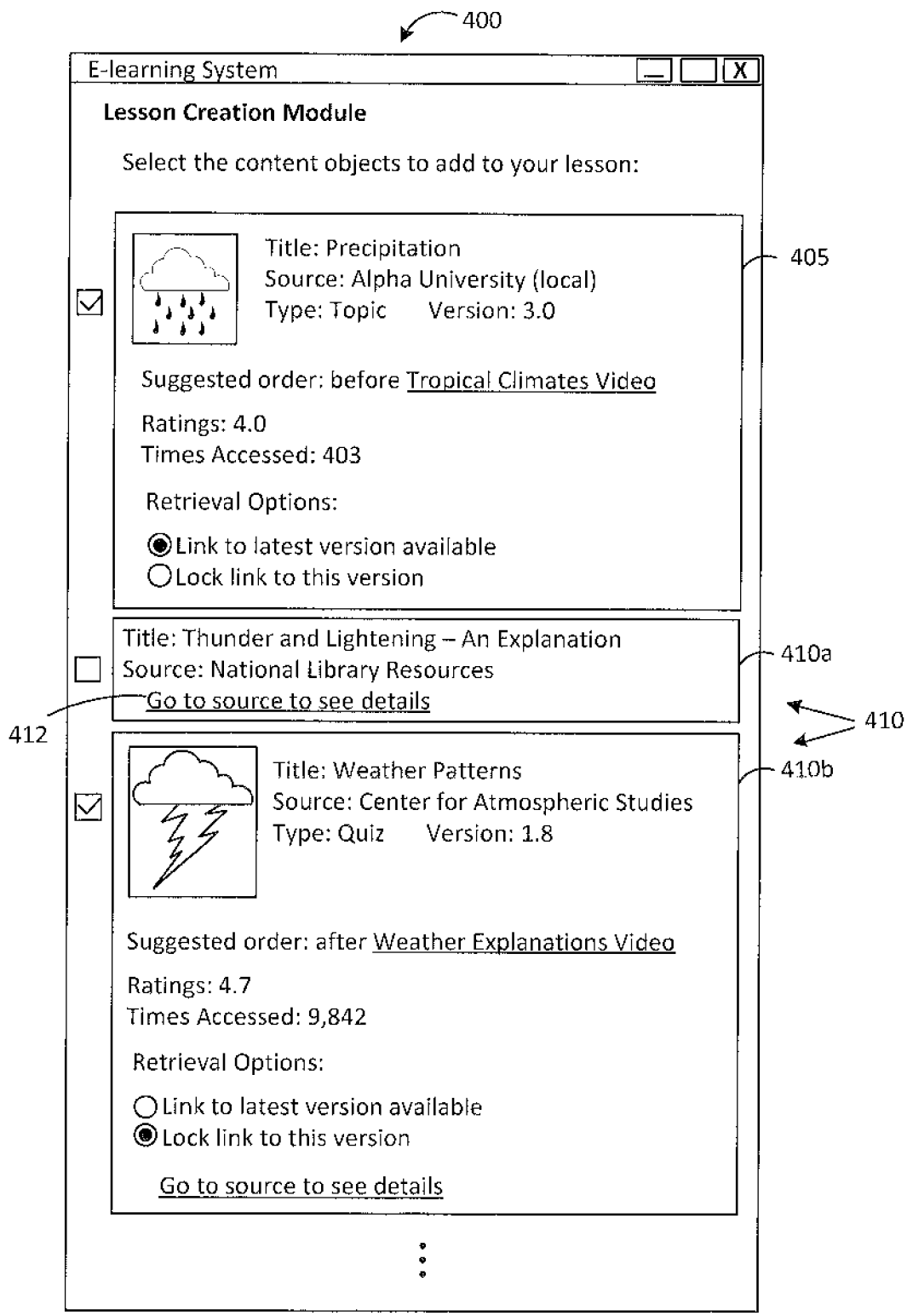
FIG. 4 is a screenshot of an example user interface showing search results that may be retrieved from the second repository, in accordance with at least one example embodiment.

Referring now to FIG. 4, shown there generally as 400 is a screenshot of an example user interface showing search results that may be retrieved from the second repository 70b, in accordance with at least one example embodiment described herein. The screenshot 400 may be displayed at the instructor device 20, for example. As shown, the screenshot is of a "Lesson Creation Module" that provides an instructor with the ability to "Select content objects to add to a lesson".

The list of content objects presented to the instructor for selection may contain both a local content object 405 that is stored locally on the second repository 70b, as well as harvested content objects 410 that are stored on repositories 70 that are remote from the second repository 70b. In other examples, there can be more or less local and harvested content objects.

For the local content object 405, the second repository 70b may be able to return search results that include information describing the learning content of the local content object 405 because the second repository 70b has local access to such information. As will be understood, a learning provider 30 may store useful information about a local content object in the repository 70b. For example, this information may include pedagogical classifications, thumbnail images, file type information, reviews and usage information and the like. The local content object 405 may thus be displayed with such information. As illustrated, the local content object 405 displays learning content information such as the LMS type of content object it is (e.g., if the content object is a 'quiz', an 'assessment', a 'topic' and the like), a 'Suggested order' (e.g., indicating whether the learning content is to be played before or after another given object), usage information (e.g., a 'Rating', a 'Times Accessed' value for the content object or other informative statistics), and retrieval options (e.g., if the content object is selected for inclusion into a course, whether the content object would be 'Always linked to the latest version' or 'locked' to the particular version that is shown). It should be known that in alternative embodiments, more or less metadata may be shown for the local content object 405 as desired. For example, the file type (e.g., whether the file is a video, a Microsoft™ PowerPoint™ file, or a PDF) may be shown.

For the harvested content objects 410, the amount of information that is displayed in the search results may differ depending on whether the repository 70a from which the content object was retrieved provided metadata describing the learning content of content object.

For example, the harvested content object 410a shown in FIG. 4 is for a harvested content object that was retrieved from a repository 70 that does not provide metadata describing the learning content of the content objects that it stores. Metadata describing the learning content would thus not be retrieved by the second repository 70b, nor would such information be provided in search results to the instructor device 20. When the harvested content object 410a is then displayed in search results, information about the learning content of the content object would not be displayed and only a simplified listing of information (e.g., that includes the 'Title' and 'Source' of the content object) would be shown. For an instructor to determine more information about the actual learning content of the content object, they may have to click on a hyperlink 412 to see more details.

If the remote repository 70 provides metadata describing the learning content of the content object, then such metadata may be retrieved by the second repository 70b when the second repository 70b is creating the harvested content object (e.g., as described above with respect to acts 315-335 in FIG. 3). The information describing the learning content could then be provided to the instructor device 20 in search results, so that a harvested content object can be displayed in a more fulsome way. In FIG. 4, the harvested content object 410b is an example of how learning content about a harvested content object 410b can be displayed. As compared with the harvested content object 410a which only shows a simple listing of information such as 'Title' and 'Source', the harvested content object 410b displays additional information relating to the learning content of the harvested learning object. For example, information about the 'LMS-Type' of the content object, the 'Suggested order' that the content object should be used in (e.g., after the 'Weather Explanations Video'), 'Usage Information' for the content object (e.g., 'Ratings' and 'Times Accessed' values for the content object), and 'Retrieval Options' for the content object are shown. Again, in alternative embodiments, other types of metadata may be stored for a harvested content object.

Therefore, in accordance with at least one of the example embodiments described herein, a harvested content object in the search results may be displayed in a manner that is substantially similar to the way in which a local content object is displayed. This may increase user convenience for an instructor because the instructor may not need to be directed to external sources (e.g., by clicking on hyperlinks) to obtain information about the learning content of a harvested content object. The increased user convenience may result in a larger number of harvested learning objects being included into online courses by instructors, thereby increasing the sharing of content objects amongst repositories 70. The present embodiments may also allow instructors to view richer content for the harvested content objects in search results, so as to enable them to create high quality courses more quickly.

Referring back to FIG. 3, in addition to simply providing information generated from the additional metadata of harvested content objects in search results, in various embodiments, the second repository 70b may be able to perform actions on the harvested content object themselves based on the additional metadata associated with the learning content (e.g., as retrieved at step 325 in FIG. 3). These actions may be the same as that which would have been performed for a local content object having the same type of metadata.

For example, it may be the case that the second repository 70b is able to automatically recognize the LMS type of a local content object, and using the LMS type information, automatically perform an action that is appropriate for the local content object of the LMS type. In one scenario, this may involve the second repository 70b automatically integrating a local content object that is of an 'assessment' type into a LMS gradebook (which may itself be another content object).

As noted, LMS type is an example of the metadata that may be retrieved for a given harvested content object at step 325 of FIG. 3. Accordingly, the second repository 70b may be able to perform the same action of automatically integrating a content object that is of an 'assessment' type into a LMS gradebook for the harvested content object also. In one example implementation, this may involve the second repository 70b: recognizing the LMS type of the harvested content object as being the LMS type of the content object (e.g., recognizing that the harvested content object is of an 'assessment' type); determining an action that can be performed for the harvested content object based on the LMS type (e.g., that the harvested content object can be integrated into a LMS gradebook); and performing the action for the harvested content object (e.g., actually integrating the harvested content object into the LMS gradebook).

Metadata Describing Learning Content Containing Links to an Interface

In various embodiments, the metadata describing the learning content that can be transmitted from a first repository 70a to a second repository 70b may contain attributes that allow the second repository 70b to interact with the first repository 70a. For example, the metadata describing the learning content for a content object stored at the first repository 70a may contain a link to an interface (e.g., an Application Programming Interface (API)) that is provided by the first repository. The interface may, for example, allow for greater interaction with the content objects stored in the first repository 70a by allowing the second repository 70b to provide information related to a harvested content object to the first repository 70a. These embodiments may, in certain situations, be considered to be ways of communicating between repositories.

For example, the metadata describing the learning content may include different options for retrieving the content object (e.g., a retrieval API). In some embodiments, this may be implemented in the form of a link (e.g., Uniform Resource Locators (URLs) that can be displayed as hyperlinks) that, when accessed, allows the second repository 70b to indicate to the first repository 70a a version of the content object the harvested content object is to refer to. In various embodiments, the link may consistently provide access to the newest version of the content object stored in the first repository 70a. Additionally, or alternatively, the metadata may include a link that is locked to the particular version of the content object that has been retrieved from the first repository 70a. If links to these URLs are included in the metadata describing the learning content of a content object, then retrieval options may be presented to an instructor when they are selecting the content object (e.g., for inclusion into an online course). An example of how retrieval options may be presented in a user interface is illustrated in the harvested content object 410b shown in FIG. 4.

Figure 5A:
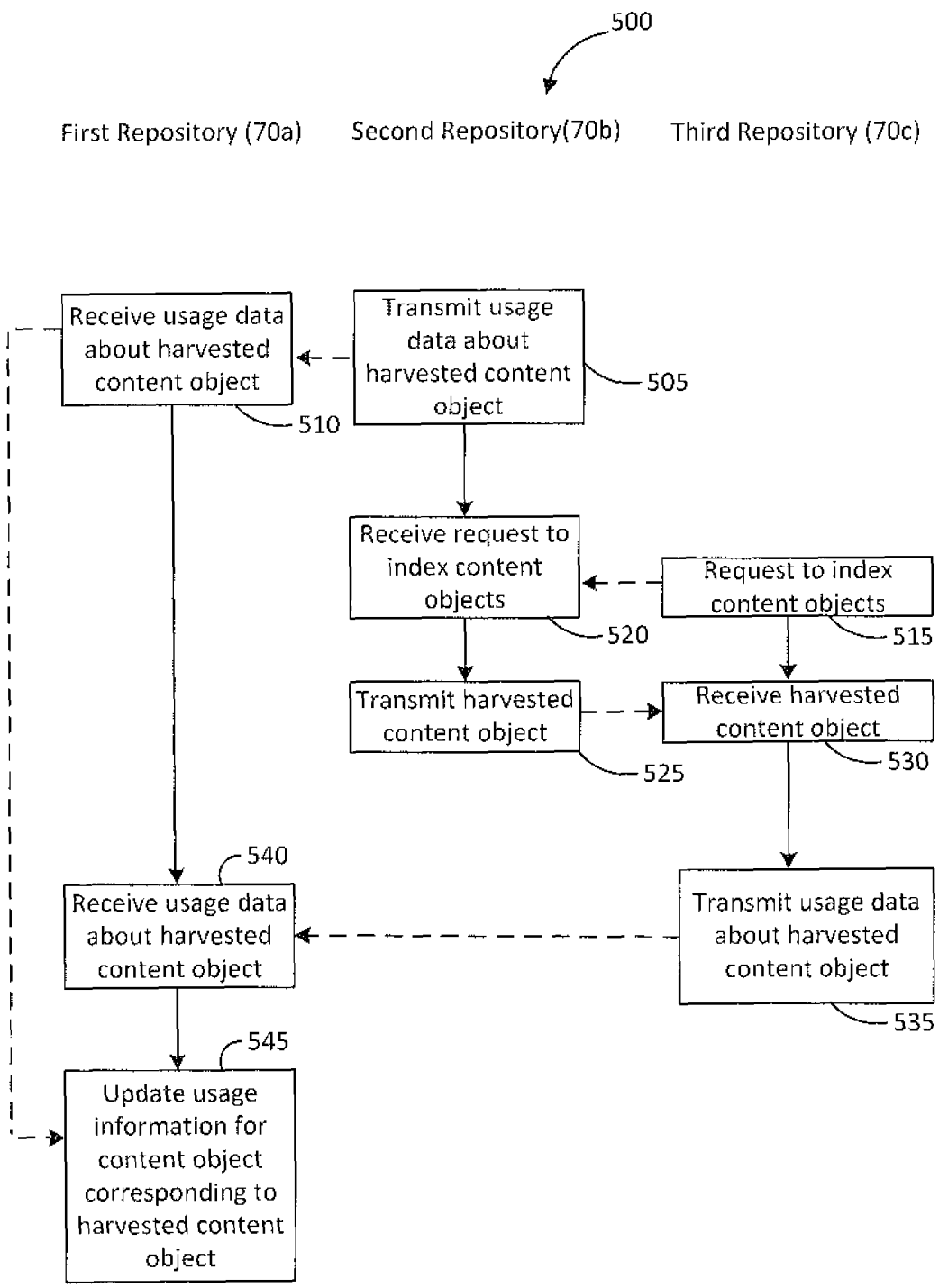
FIGS. 5A and 5B are flow chart diagrams illustrating example interactions between a first repository, a second repository, and a third repository, when the second and third repositories provide usage data to the first repository, in accordance with at least one example embodiment.

Referring now to FIG. 5A, shown there generally as 500 is a flow chart diagram illustrating interactions between a first repository, a second repository, and a third repository, when the second and third repositories provide usage data to the first repository, in accordance with at least one example embodiment described herein. FIG. 5A uses terminology similar to that which is used in FIG. 3. A first repository 70a stores the content object which may be harvested by the second repository 70b. The acts shown in FIG. 5A may be performed at any time after the content object stored on the first repository 70a has been harvested by the second repository 70b (e.g., after acts 305-335 in FIG. 3).

In FIG. 5A, the metadata describing the learning content of a content object may include a link to an API that, when accessed, allows usage data about the content object to be transmitted back to the first repository 70a.

At 505, the second repository 70b may transmit usage data about the harvested content object to the first repository 70a. For example, the second repository 70b may be able to collect usage data about how the harvested content object is being used in the educational system 10 (as shown in FIG. 1). In various embodiments, the type of usage data that is collectable by the second repository 70b may be of the same type that the first repository 70a would collect if the content object was being accessed locally from the first repository 70a.

For example, as discussed above, usage data may generally include information such as comments, reviews, feedback, numerical rating(s) and/or other information that indicates a user's impressions of the quality, difficulty, or relevance of the content object. Additionally or alternatively, usage data may also include information about the users of a content object such as the instructor(s) who are using the content object, student(s) who are able to access the content object, listings or links to particular course(s) that include the content object, and/or the institution(s) using the content object.

When using a given content object, a computing device 20 may be able to solicit such user feedback information by displaying a prompt after a harvested content object has been used.

At 510, the usage data about the harvested content object, as transmitted from the second repository 70b, may be received at the first repository 70a.

Conventionally, the first repository 70a would not have a way of determining how a content object is used once it has been harvested by the second repository 70b. By providing a mechanism that allows the "recipient" second repository 70b to communicate usage data about the harvested content object back to the "source" first repository 70a, the first repository 70a may be able to update the usage information that it stores for the content object. As shown, the method 500 may proceed to 545 (as shown with a dotted line), where the first repository 70a may take the usage data received from the second repository 70b or another repository, and use it to update the usage information it stores for the corresponding content object.

In various embodiments, a third repository 70c may be configured to index and retrieve content objects from the second repository 70b, and the third repository 70c may also be able to communicate usage data to the first repository 70a. Steps 515-540 elaborate on these embodiments in greater detail.

At 515, the third repository 70c may request to index content objects available from the second repository 70b. At 520, the second repository 70b may receive the request to index the content objects.

At 525, the second repository 70b may transmit a harvested content object to the third repository 70c. As will be understood, when a given repository 70 is indexed by another repository 70, the repository 70 being indexed may allow both local and harvested content objects stored on it to be retrieved by the other repository. For example, in FIG. 5A, if the second repository 70b is being indexed by the third repository 70c, the third repository 70c may be able to retrieve content objects that are local to the second repository 70b, as well as harvested content objects that the second repository 70b has retrieved from the first repository 70a or other repositories.

At 530, the third repository 70c may receive the harvested content object from the second repository 70b. Notably, the harvested content object received by the third repository 70c may contain the same metadata describing the learning content of the content object as retrieved by the second repository 70b. For example, the metadata of the harvested content object received by the third repository 70c may also include the link to the usage data API that, when accessed, allows the third repository 70c to communicate usage data about the harvested content object (as generated at the third repository 70c) to the first repository 70a.

Using this data usage API, at 535, the third repository 70c may then transmit usage data about the harvested object to the first repository 70a. The usage data transmitted by the third repository 70c may be similar to that which can be transmitted by the second repository 70b discussed above.

At 540, the first repository 70a receives usage data about the harvested content object from the third repository 70c. At 545, the first repository 70a may then update the usage information it stores for the content object corresponding to the harvested content object, with the usage data it received from the third repository 70c.

Figure 5B:
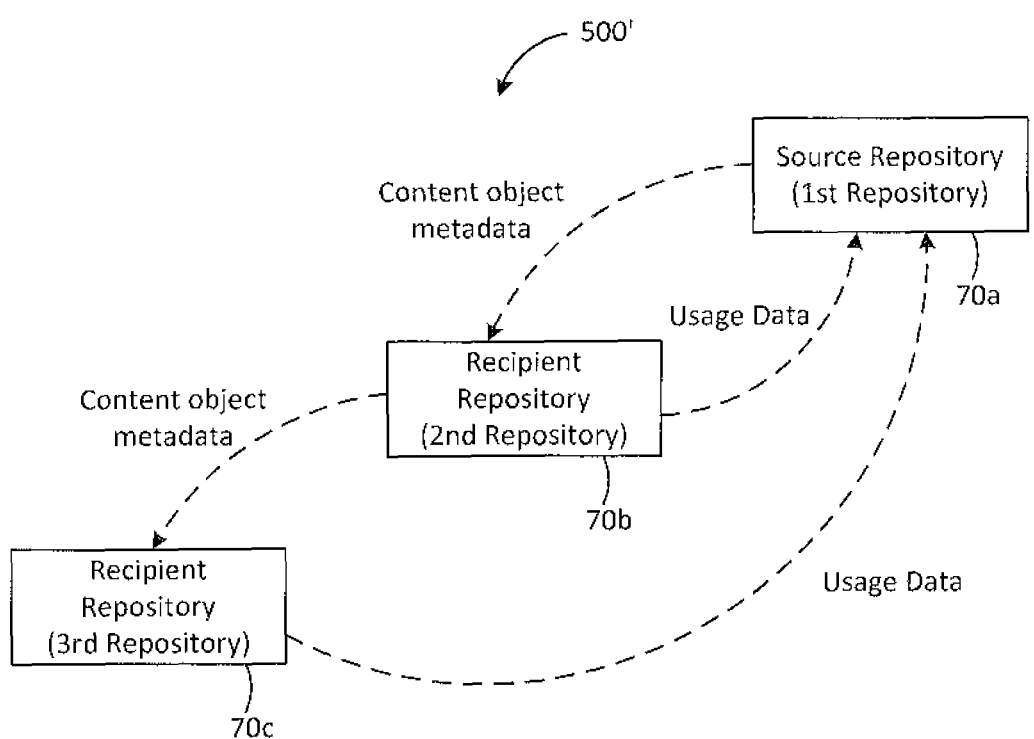

Referring now to FIG. 5B, shown there generally as 500' is another flow chart diagram illustrating interactions between a first repository, a second repository, and a third repository, when the second and third repositories provide usage data to the first repository, in accordance with at least one example embodiment described herein. The embodiment illustrated in FIG. 5B is a simplified form of the method shown in FIG. 5A in that only the data flow amongst the first, second, and third repositories are shown. As illustrated in FIG. 5B, the first repository 70*a* is labeled the "source" repository because it stores the original content object. The second repository 70*b* and the third repository 70*c* are labeled "Recipient" repositories because they store harvested content objects corresponding to the content object stored on the first repository 70*a*. As discussed above with respect to FIG. 5A, content object metadata (e.g., describing the learning content of the content object stored on the first repository 70*a*) may be provided from the first repository 70*a* to the second repository 70*b*, and also from the second repository 70*b* to the third repository 70*c*. The transmission of this metadata is shown in FIG. 5B with the dotted arrows from the first repository 70*a* to the second repository 70*b*, and from the second repository 70*b* to the third repository 70*c*.

Since each of the harvested content objects stored on the second repository 70*b* and the third repository 70*c* may store a link to the usage data API provided on the first repository 70*a*, the second repository 70*b* and third repository 70*c* may then transmit usage data for their respective harvested content objects back to the first repository 70*a*. This is shown in FIG. 5B with the dotted arrows from the second repository 70*b* to the first repository 70*a*, and from the third repository 70*c* to the first repository 70*a*.

While not explicitly illustrated, the harvested content object stored on the third repository 70*c* may itself be further harvested by yet another repository 70. As will be understood, such harvesting of harvested content objects may be repeated any number of times with the result being that all such recipient repositories 70 contain a harvested content object that contain a link to the usage data API provided on the source repository 70*a*. In this manner, all recipient repositories 70 that store a harvested content object corresponding to the content object stored on the first repository 70*a* may be able to communicate with the first repository 70*a* to provide usage data about how the harvested content object is being used at that particular recipient repository 70.

In some embodiments, the usage data stored on each of the first repository 70*a*, second repository 70*b*, and third repository 70*c* (and any further recipient repositories 70, as the case may be) can be kept synchronized. For example, the usage data transmitted from the recipient repositories (e.g., second repository 70*b* and third repository 70*c*) to the first repository 70*a* may be of the same type as that which was transmitted from the first repository 70*a* to the recipient repositories 70 when the harvested content object was first created. If this same type of data is transmitted back to the first repository 70*a*, the first repository 70*a* may be able to subsequently send an update to the second repository 70*b* with updated usage information that takes into account the usage data received by the first repository 70*a*.

When sending this updated usage data, the transmission may again be formatted according to the metadata structure that was originally used to transmit the usage data to the second repository 70*b* when the harvest content object was created. Similarly, once this data has been received at the second repository 70*b*, the second repository 70*b* may be configured to send an update to the third repository 70*c* that retrieved the harvested content object from the second repository 70*b*. In this manner, the usage information may be able to be kept synchronized across all repositories that store the content object (regardless of whether the content object is stored locally as a local content object or as a harvested content object). By keeping usage information updated at all repositories, if yet an additional repository attempts to retrieve a harvested content object from any of the repositories 70*a*, 70*b*, 70*c*, then the most accurate usage data is provided to that additional repository.

The synchronization of the usage information amongst various repositories that access the content object may promote a more holistic and global learning community. For example, such a global learning community may allow users and potential users of the content objects to obtain a more accurate depiction of the quality and/or usefulness of a given content object because usage data is obtained from a broader range of users of the content object. This may be desirable over existing repository systems in which traditional publishers simply provide their content objects in isolation, without as accurate an indication of the quality and/or usefulness of the content object.

In various embodiments, instead of the second repository 70*b* forwarding the updated usage information to the third repository 70*c* along the same communication path in which the content object was harvested, the third repository 70*c* (or any other recipient repository 70 storing a harvested content object) may be able to receive the updated usage information directly from the first repository 70*a*. For example, the first repository 70*a* may provide an API that allows a recipient repository 70*b*, 70*c* to register itself with the first repository 70*a* for receiving direct updates from the first repository 70*a*. In such embodiments, a link to that API may be included in the extended metadata for a content object provided at the first repository 70*a*, so that a recipient repository 70*b*, 70*c* harvesting the content object would receive the link to the API. The recipient repository 70*b*, 70*c* may then access the API via the link to register itself with the source repository 70*a*. When registering a recipient repository 70*b*, 70*c*, the first repository 70*a* may add the recipient repository 70*b*, 70*c* to a list of repositories 70 that are to receive updates from the source repository 70*a*. Subsequently, when an update becomes available, the repository 70*a* may then refer to the list to identify the recipient repositories 70*b*, 70*c* to send the update to.

In various embodiments, the updated usage data may be provided to a recipient repository 70 in a number of ways. For example, the recipient repository 70 may poll the repository 70 from which they retrieved the harvested content object for updates (e.g., repository 70*a* or repository 70*b*, as the case may be), and the updated usage data may be provided in response. In various embodiments, the updated usage data may be provided alongside other updates that are also to be provided to a given harvested content object. Additionally, or alternatively, repositories 70 may be configured to track the external repositories that have harvested a content object from it, and push the updated usage data to those external repositories when the updated usage data becomes available.

Referring now to FIG. 6, shown there generally as 600, is an example of learning content in the form of an XML file that may be provided by a first repository, in accordance with at least one example embodiment. As noted above, the first repository 70*a* can be configured to transmit a harvested content object using an XML schema for a modified version of the OAI-PMH protocol that extends the traditional metadata items provided by the protocol.

As illustrated, the example XML file shown in FIG. 6 contains a number of conventional elements that may be used in the OAI-PMH protocol to describe the subject matter of a content object. As will be understood by those skilled in the art, a standardized vocabulary called "Dublin Core" containing a number of the shown elements has been developed, and these elements may be used in the OAI-PMH protocol. In the example shown, an example image is described using XML data elements, and data for a number of the Dublin Core elements have been provided. Specifically, data for the creator 604, description 606, format 608 (e.g., a file format of a media type such as Joint Photographic Experts Group (JPEG)), rights 612 (e.g., copyright rights that may attach to the content object), source 610 (e.g., indicating a URL of where the content object is located), subject 614, and title 616 have been provided.

Additionally, FIG. 6 also shows data elements that extend beyond the data elements traditionally provided by the OAI-PMH protocol. These elements describe the learning content of the content object, so that the learning content of the content object can be harvested and subsequently accessed from the second repository 70b and/or the third repository 70c, for example so that the information can be displayed in search results (such as the example shown in FIG. 4). As illustrated, the extended data elements that describe the learning content include data for a 'thumbnailUrl' 618 which provides a URL for the location of a thumbnail image representing the content object, an 'ImsType" 620, a related object 622 data element which contains data relating to how the content object may be related to other content objects (e.g., as shown, there are sub-elements that show the URL for where the parent topic of the image in the content object is located), and a 'usageData' 624 data element which contains data for the usage information of the content object (e.g., the 'Ratings' sub-element and the 'TimesAccessed' sub-element), as well as a 'reviewsUrl' sub-element that provides a link to an API that a recipient repository can access to communicate usage data back to the source repository for the content object.

Referring now to FIGS. 7A and 7B, shown there generally as 700 is an example of a schema file that indicates how the data in the XML file of FIG. 6 may be structured, in accordance with at least one example embodiment described herein. As will be understood by those skilled in the art, a schema file may indicate to a given recipient repository 70 the data elements that are available in a given XML file that describes a content object, and how the XML file may be processed.

For example, as shown in FIG. 7A, there is a controlled vocabulary for the 'ImsType' 720 (e.g., the 'Learning Management System-type') data element which indicates the types of LMS data that can be harvested (e.g., content objects which are a 'Course', a 'Topic', a 'Quiz', a 'Discussion', etc.). Also, there is a 'usageData' 724 descriptor that indicates what the sub-elements within the 'usageData' data element are, and how they can be processed. Similarly, there is an 'objectRelation' descriptor 722 that indicates how content objects can be related to one another.

Referring now to FIG. 7B, shown there is the remaining portion of the schema shown in FIG. 7A. A list of the conventional 'Dublin Core' data elements 750 are indicated as being inherited from the 'Dublin Core' vocabulary used in conventional metadata harvesting methods. Also, some of the learning content-specific data elements 760 that extend the conventional 'Dublin Core' elements are listed at the end of the schema file.

Notably, in various embodiments, the structure of the metadata for a harvested content object can include additional or fewer elements than the ones shown and discussed with respect to FIGS. 6, 7A and 7B. For example, the harvested content object can additionally include a section field (not shown) for indicating the sections or chapters found in the content object. Similarly, a harvested content object may omit the 'thumbnailUrl' field if a content object does not contain any images or multimedia content. It will also be understood that the contents of the schema that indicates the structure of the metadata describing the learning content may be adapted to suit the particular features of the learning content of the content objects that is desired to be harvested.

In the above discussion, the information about a content object communicated from a second repository (or a third, fourth, or subsequent repository, as the case may be) to a first repository were discussed in the context of a learning environment where repositories were providing learning objects. It will be appreciated, however, that the metadata that allows such communication to occur could be included in any type of content objects provided by any type of repository.

For example, there may be repositories of a general nature (e.g., for entertainment or commercial purposes) that are storing content objects that can be indexed and harvested by other repositories. The present embodiments may allow content objects stored in such repositories to include metadata that includes a link to an interface provided by those repositories. When the metadata is harvested by another repository, the link may then be accessible by the other repository to communicate information about the harvested content object back to the first (source) repository.

It will be understood that the link may provide access to any type of interface that is desirable for a content object. For example, depending on the nature of the content object, it may be desirable for the source repository to obtain information about the number of times the content object appears in search results at a given recipient repository. Accordingly, an interface may be provided for receiving such information at the source repository, and a link to that interface may be included in the metadata for that content object. A recipient repository may then be able to track this information, and the recipient repository may access the interface to provide such information back to the source repository. It will be appreciated that additional types of interfaces may be possible.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the subject matter described herein and non-limiting and it will be understood by persons skilled in the art that other variants and modifications may be made without departing from the scope of the subject matter as defined in the claims appended hereto.

For example, the steps of a method in accordance with any of the embodiments described herein may be performed in any order that provides a useful result, whether or not such steps are described in the claims, figures or otherwise in any sequential numbered or lettered manner. Also, in the various user interfaces illustrated in the figures, it will be understood that the illustrated user interface text and controls are provided as examples only and are not meant to be limiting. Other suitable user interface elements may be possible.

In addition, as used herein, the wording "and/or" is intended to represent an inclusive-or. That is, "X and/or Y" is intended to mean X or Y or both X and Y. Moreover, "X, Y, and/or Z" is intended to mean X or Y or Z or any combination thereof.

The invention claimed is:

1. A method of obtaining metadata for content stored in a first repository, the method to be performed at a second repository, the method comprising:
   identifying a content object stored in the first repository, the content object comprising learning content usable in an electronic educational system to provide electronic learning;
   identifying metadata for the content object stored in the first repository, the metadata associated with the learning content of the content object;
   retrieving the metadata associated with the learning content from the first repository;
   storing a harvested content object corresponding to the content object, wherein the harvested content object comprises the metadata associated with the learning content of the content object stored in the first repository, wherein the harvested content object comprises one or more types of metadata that are not stored by the first repository with regard to the content object; and
   communicating usage data about the harvested content object to the first repository such that usage information for the content object stored at the first repository is updatable based on the usage data about the harvested content object.

2. The method of claim 1, further comprising:
   generating information from the metadata associated with the learning content of the content object; and
   if the harvested content object is located in a search for content objects performed at the second repository, providing the generated information along with the harvested content object in the search results so that when the search results are displayed, the generated information for the harvested content object is displayed in the same manner as when corresponding information is displayed for local content objects stored at the second repository.

3. The method of claim 1, wherein the retrieving of the metadata is performed using a modified version of the Open Archives Initiative Protocol for Metadata Harvesting (OAI-PMH) protocol, the modified version comprising an Extensible Markup Language (XML) schema that extends metadata items provided in the OAI-PMH protocol to include the metadata associated with the learning content.

4. The method of claim 1, wherein the learning content comprises a Learning Management System (LMS) type of the content object.

5. The method of claim 4, further comprising:
   recognizing the LMS type of the harvested content object as being the LMS type of the content object;
   determining an action that can be performed for the harvested content object based on the LMS type; and
   performing the action for the harvested content object.

6. The method of claim 5, wherein the LMS type comprises an assessment, and wherein the action comprises integrating the harvested content object into a LMS gradebook.

7. The method of claim 5, wherein the action is the same as that which would be performed for a local content object that is also of the LMS type, stored at the second repository.

8. The method of claim 1, wherein the learning content comprises usage information for the content object.

9. The method of claim 1, wherein the learning content comprises relationship information for the content object with respect to one or more other content objects.

10. The method of claim 9, wherein the relationship information for the content object comprises structure information that indicates that the content object contains, or the content object is contained within, the one or more other content objects.

11. The method of claim 9, wherein the relationship information for the content object comprises sequence information that indicates that the content object is recommended to be used before or after the one or more other content objects.

12. The method of claim 9, wherein the relationship information for the content object comprises information indicating that the content object and the one or more other content objects are members of a same collection of content objects.

13. The method of claim 1, wherein the learning content comprises at least one of: information indicating an instructor using the content object; information about a student who is able to access the content object; information indicating a course using the content object; and information indicating an institution using the content object.

14. A non-transitory computer-readable medium storing instructions for obtaining metadata for content stored in a first repository, wherein when the instructions are executed by a processor of a server hosting a second repository, the processor is configured to:
   identify a content object stored in the first repository, the content object comprising learning content usable in an electronic educational system to provide electronic learning;
   identify metadata for the content object stored in the first repository, the metadata associated with the learning content of the content object;
   retrieve the metadata associated with the learning content from the first repository;
   store a harvested content object corresponding to the content object, wherein the harvested content object comprises the metadata associated with the learning content of the content object stored in the first repository, wherein the harvested content object comprises one or more types of metadata that are not stored by the first repository with regard to the content object; and
   communicate usage data about the harvested content object to the first repository such that usage information for the content object stored at the first repository is updatable based on the usage data about the harvested content object.

15. A server comprising:
   a memory that is configured to store instructions for hosting a second repository that obtains metadata for content stored in a first repository; and
   a processor that is coupled to the memory, the processor being configured to execute the instructions, identify a content object stored in the first repository, the content object comprising learning content usable in an electronic educational system to provide electronic learning; identify metadata for the content object stored in the first repository, the metadata being associated with the learning content of the content object; retrieve the metadata associated with the learning content from the first repository; store a harvested content object corresponding to the content object, wherein the harvested content object comprises the metadata associated with the learning content of the content object stored in the first repository, wherein the harvested content object comprises one or more types of metadata that are not stored by the first repository with regard to the content object; and communicate usage data about the harvested content object to the first repository such that usage information for the content object stored at the first repository is updatable based on the usage data about the harvested content object.

16. The server of claim 15, wherein the processor is further configured to:
   generate information from the metadata associated with the learning content of the content object; and
   if the harvested content object is located in a search for content objects performed at the second repository, to provide the generated information along with the harvested content object in the search results so that when the search results are displayed, the generated information for the harvested content object is displayed in the same manner as when corresponding information is displayed for local content objects stored at the second repository.

17. The server of claim 15, wherein the retrieving of the metadata is performed using a modified version of the Open Archives Initiative Protocol for Metadata Harvesting (OAI-PMH) protocol, the modified version comprising an Extensible Markup Language (XML) schema that extends metadata items provided in the OAI-PMH protocol to include the metadata associated with the learning content.

18. The server of claim 15, wherein the learning content comprises a Learning Management System (LMS) type of the content object.

19. The server of claim 18, wherein the processor is further configured to:
   recognize the LMS type of the harvested content object as being the LMS type of the content object;
   determine an action that can be performed for the harvested content object based on the LMS type; and
   perform the action for the harvested content object.

20. The server of claim 19, wherein the LMS type comprises an assessment, and wherein the action comprises integrating the harvested content object into a LMS gradebook.

* * * * *